United States Patent [19]

Keith, Jr.

[11] 4,030,370
[45] June 21, 1977

[54] TRANSDUCER POSITIONER FOR TESTING TUBES FROM INSIDE DIAMETER

[75] Inventor: Thomas R. Keith, Jr., Ponca City, Okla.

[73] Assignee: Continental Oil Company, Ponca City, Okla.

[22] Filed: Feb. 25, 1976

[21] Appl. No.: 661,192

[52] U.S. Cl. .................... 73/67.8 S; 73/71.5 US
[51] Int. Cl.² ................................. G01N 29/04
[58] Field of Search ......... 73/67.8 R, 67.8 S, 67.9, 73/71.5 US

[56] References Cited
UNITED STATES PATENTS

| | | | |
|---|---|---|---|
| 3,021,706 | 2/1962 | Cook et al. | 73/67.8 S |
| 3,741,003 | 6/1973 | Gunkel | 73/71.5 US |
| 3,952,581 | 4/1976 | Gottelt | 73/67.8 S |

FOREIGN PATENTS OR APPLICATIONS 1,172,385  11/1969  United Kingdom .......... 73/71.5 US Primary Examiner—Richard C. Queisser
Assistant Examiner—John P. Beauchamp
Attorney, Agent, or Firm—Cortlan R. Schupbach, Jr.

[57] ABSTRACT

A transducer positioner for testing conduits from the interior comprising a standard pulse-echo ultrasonic instrument converted to a detection package comprising a. a head which positions at least two transducers simultaneously
b. a connecting tube to provide a water column for coupling each transducer to the conduit to be tested
c. connecting cables from each transducer to the ultrasonic source instrument, and
d. a terminal box containing connectors and a calibration transducer.

6 Claims, 9 Drawing Figures

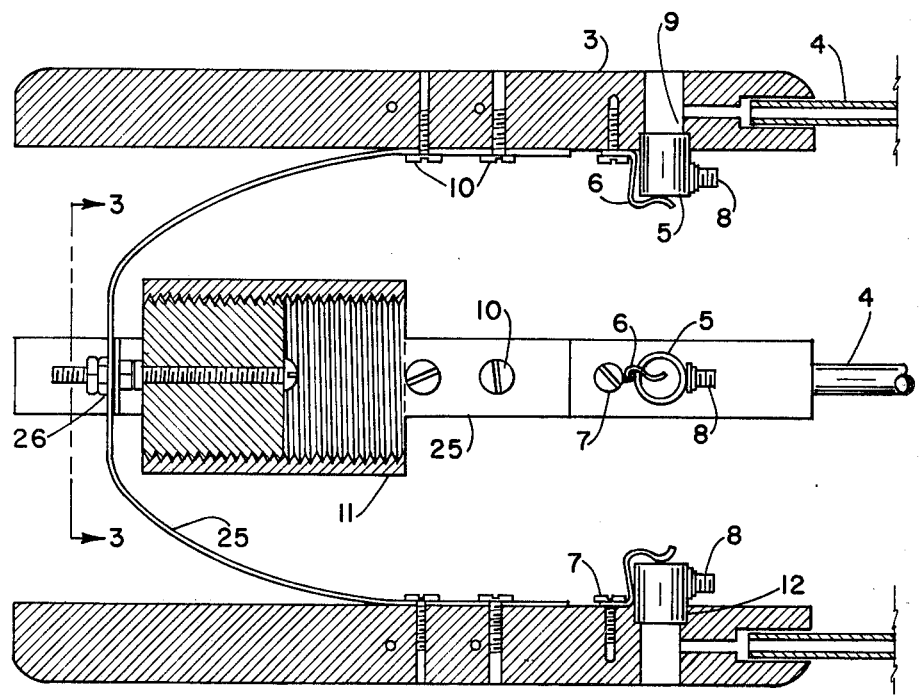
FIGURE 2
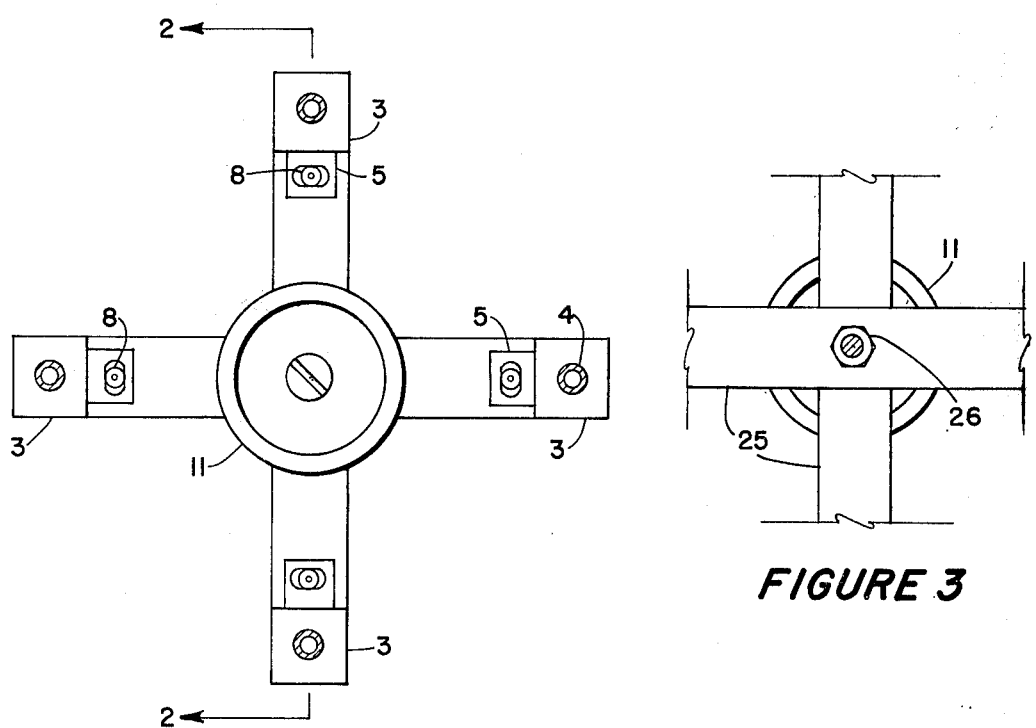
FIGURE 1
FIGURE 3

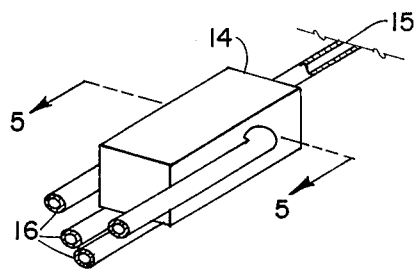
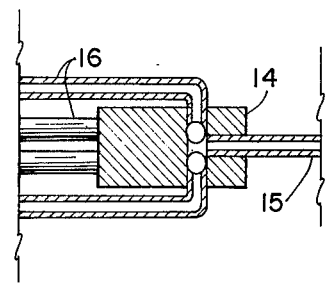
FIGURE 4          FIGURE 5
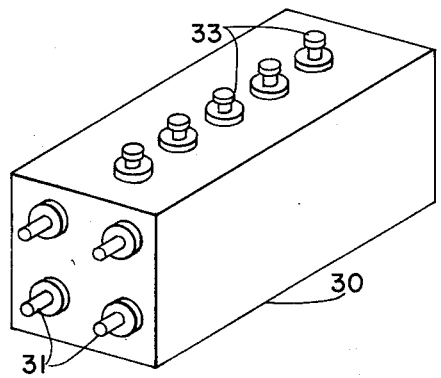
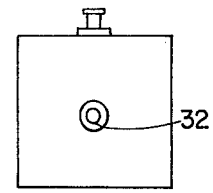
FIGURE 6          FIG. 7
FIGURE 8
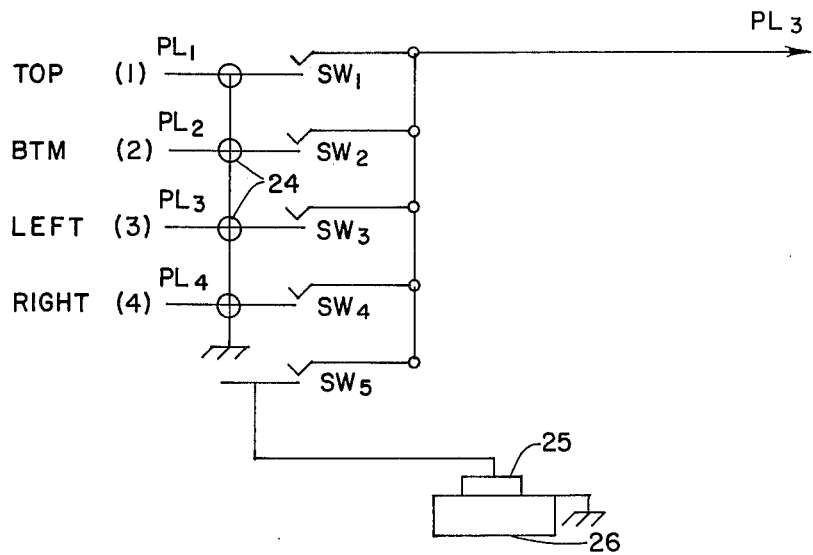
FIGURE 9

TRANSDUCER POSITIONER FOR TESTING TUBES FROM INSIDE DIAMETER

This invention relates to an apparatus for testing conduits from the interior of said conduits, more particularly, this invention comprises a transducer positioner allowing water coupling of the conduits from the interior and accurate testing of such conduits.

The prior art has long been aware of the advantages of testing wall thicknesses and quality of conduits using ultrasonic instruments. For example, U.S. Pat. No. 3,600,613 teaches a transducer probe for ultrasonic pulse echo testing comprising a circular elongated body which is inserted into tubing rotated during the test while actually moving through the conduit. U.S. Pat. No. 3,810,384 teaches a self-propelled ultrasonic instrumentation package which travels through pipelines. U.S. Pat. No. 3,415,111 shows an apparatus for testing tubes or rods by ultrasonic means; however, the apparatus is on the exterior of the pipe. U.S. Pat. No. 3,896,662 also teaches means for using ultrasonic sound waves to check tubular structures for wall thickness, concentricity, and straightness, etc. Many other patents are in the area such as that issued at U.S. Pat. No. 3,404,551, which teaches a method of testing pipe from the exterior portions.

However, these inventions individually and in combination have been unsatisfactory for many purposes. For example, when boiler tubes are being tested for fitness and further use, it has been impossible in many cases to test the tubes from the exterior portion due to the clustering of tubes and physical space limitations; however, testing such conduits from the interior has also presented problems. For example, a probe such as that described in U.S. Pat. No. 3,600,613 cannot intimately contact the walls, which in many cases are pitted and corroded from continued use. In addition, such probes are limited to one size of conduit and are inflexible as to areas of use. It is therefore an object of the present invention to provide a method for overcoming these difficulties.

It is therefore an object of the present invention to provide an apparatus for testing tubes from inside diameter which are normally inaccessible to other means. Other objects will become apparent to those skilled in this art as the description proceeds.

In accordance with the present invention, there has been developed a positioner for passing transducers through tubes from the inside diameter while forming an intimate connection with the interior wall and allowing accurate readings to be made therefrom. The invention can be more completely described by stating that it comprises a transducer positioner for testing conduits from the interior utilizing standard pulse-echo ultrasonic equipment converted to a detection package comprising (a) a head which positions at least two transducers simultaneously, (b) a connecting tube to provide a water column for coupling each transducer to the conduit to be tested, (c) connecting cables from each transducer to the ultrasonic source instrument, and (d) a terminal box containing connectors and a calibration transducer. It will be readily apparent that the above-described positioner has many advantages over those methods described in the prior art. Multiple transducers can be drawn through the tube simultaneously thus allowing readings over a larger area of the conduit. When connected to a rigid motive means, the transducer package may optionally be rotated, or drawn through the conduit without rotation as it proceeds along the longitudinal axis of the conduit. Pitting and corrosion of the interior of the conduit will not affect the accuracy of the readings at any given point since a water couple is utilized, allowing intimate connection to be made with the wall at all points. Thus the objections inherent in the prior art apparatus have been overcome.

The figures describe an apparatus actually constructed and tested.

FIGS. 1 through 3 indicating various views of the sub-assembly which is passed through the interior of a conduit, FIGS. 4 and 5 illustrating the water header used to provide water coupling to the sub-assembly, FIGS. 6 and 7 showing the switching apparatus used to take readings from the various transducers, and FIGS. 8 and 9 showing the connecting assembly and the switching apparatus used in the model actually built.

The invention can be more completely described and understood with reference to the attached drawings. In FIG. 2 an overall view of the complete assembled positioner containing four shoes, each having one transducer, is shown. The individual shoes are mounted on flat, leaf-type springs which are connected at one point to form a cup-like effect. (1) The springs may be optionally extended to a second connection in order to provide greater rigidity if desired. The individual shoes themselves (3) each contain a conduit for water (4) and a transducer (5). Each transducer, in addition, has a connection (8) leading to the ultrasonic source instrument. The entire assembled positioner comprising transducers, spring means, shoes, and motive connection means is hereafter referred to as a head.

The individual shoes are also described with reference to FIG. 2 wherein (3) refers to the material of the shoe itself. This material, in the actual model built, was of Plexiglas, but tended to wear rather quickly. Other materials useful in the practice of the instant invention would be stainless steel, steel of various types, polyesters, and the various plastics, if marring of the conduit interior be avoided. For example, a tetrafluoro-hydrocarbon shoe would have very little friction, would wear fairly well, and would not mar the interior of many conduits. The shoe is attached to the spring positioner means by a fastening means (10). The fastening can be accomplished by any of several well known methods, such as screws, bolts, clamps, welding, and so forth. The term "shoe" as used herein describes the entire sub-assembly which contacts the interior of the conduit, contains water coupling means, operably positions at least one transducer, and is connected to a flat leaf-type spring means which maintains intimate contact between the conduit's interior and the shoes.

The transducer (5) is retained in position by a spring clip (6) which is connected (7) by an attaching means to the shoe. The transducer operates through a water coupling passing through the interior of the shoe through a conduit (4). The opening through the interior is drilled to meet the opening over which the transducer is placed (9). The opening in which the transducer is placed (12) connects to the more narrow opening (9) through the shoe beneath the transducer (5) itself. Water flows continuously down the tube, past the transducer, and makes contact with the wall of the conduit. The individual transducer is activated and ultrasound is transmitted through the water to the wall allowing multiple reflections between the wall surfaces to be measured by the ultrasonic thickness measuring instrument. FIG. 2 describes a cross-sectional view as viewed along section lines 2—2 in FIG. 1.

FIG. 1 is an end view of the positioner along as viewed in direction 3—3 in FIG. 2 showing the shoes (3), water connections (4), coaxial cable connections (8), the transducers (5), and a motive means connection (11). The means shown is a threaded socket designed to receive a threaded pipe or bar, but clearly a cable or flexible means could be utilized equally well, should the apparatus be pulled through the conduit or the conduit be curved.

FIG. 3 is an opposite end view of FIG. 1, showing the spring means (25), the motive means connection (11), and a binding means (26) to connect the spring means to the motive means connector. Such means could of course have opposing motive means connections, in order that the apparatus be passed through the conduit by either pulling or pushing.

The water is fed to the shoes through a water header and thus identical pressure is maintained in each tube. The water header is described in FIG. 4 wherein (14) is the water header itself, (15) is the main water supply, and (16) is a plurality of tubes leading to the transducer shoes.

FIG. 5 is a section at right angles of the water header along the section lines 5—5, showing the interior configuration of the header including duct 15.

FIG. 6 is an elevated view of the switching box whose circuity is shown in FIG. 9. The switching box itself (30) contains cable connectors (31) which lead, through the coaxial cable, to the transducers inside the conduit. The reverse view, FIG. 7, shows the cable connector (32) leading to the reference transducer. The switches (33) on the top of the switch box allows the selected transducer to take readings as desired.

FIG. 8 shows a single transducer and cable assembly; (20) refers to the transducer itself which is connected to a coaxial cable through a microdot connector (21). The cable (22) leads to a cable connector (23) which in turn will allow a reading to be made on the transducer.

The switching and cable apparatus is shown in FIG. 9 wherein for a four-shoe positioner the arrangement of switches (24), reference transducer (25), and test block (26) is shown. It will be apparent to those skilled in this art that other switching apparatus such as those for simultaneous readings can be employed; however, the apparatus shown has been actually tested and has been shown to be quite effective in taking sequential readings.

The transducer positioner is first placed into the conduit to be tested. The positioner can be mounted on a cable, a pipe, or other suitable means for drawing or pushing the shoe through the conduit. The shoe is stopped at various places and various readings are taken from the wall of the conduit and referred to a test block which gives a calibration reading.

The transducers used in the operation of the test instrument were one-quarter inch, 5 megahertz transducers. The transducers were connected to the ultrasonic instrument through a microdot connector and a RG-177a/u coaxial cable to a switching assembly which allowed each individual transducer to be connected to the ultrasonic instrument independently. An additional transducer mounted on a 0.30-inch steel calibration block allowed instrument calibration without the need to detach the cable assembly. The switches used were single pole, single throw, normally off momentary switches. All plugs used were BNC coaxial connectors.

As will be apparent to those skilled in this art, many materials can be substituted for those used in the actual instrument described herein. However, the basic concept of testing conduits from the interior using a positioner containing a plurality of transducers and water coupling will not be affected by the substitution.

This apparatus has been successfully used for inspection of furnace tubes such as those in refineries and boilers. It will be readily apparent that the advantage conferred by the instant invention far supercedes that taught by the prior art. Such conduits can be inspected without removal and without respect to their outside diameter or the surrounding environment. The water coupling feature of the instant invention allows an accurate reading of walls which are uneven, such as caused by corrosion or scale.

The apparatus can be used on conduits having varying internal diameters. Usually conduits from 1 inch to 10 inches will be tested using this apparatus, but conduits having from 2 inches to 6-inch inside diameter are most easily tested. The apparatus can of course be constructed for larger conduits by constructing larger spring means and can contain as many transducer-containing shoes which can be accommodated by the interior of the conduit.

While certain embodiments and details have been shown for the purpose of illustrating this invention, it will be apparent to those skilled in this art that various changes and modifications may be made herein without departing from the spirit or the scope of the invention.

I claim:

1. A transducer positioner for testing conduits from the interior using a pulse-echo ultrasonic instrument comprising
   a. a detection head comprising
      1. flat, leaf-type springs connected in a cup-shaped arrangement,
      2. said springs supporting transducer shoes, having,
      3. a transducer attached to said shoe, said transducer being exposed to water coupling means with the conduit to be tested,
   b. connecting tubes between a water source and shoes to provide a water column for coupling each transducer to the conduit to be tested,
   c. a switching box and a calibration transducer,
   d. connecting cables from each transducer to an ultrasonic instrument, said cables passing through said switching box, said switching box allowing readings to be taken from any transducer.

2. A positioner as described in claim 1 wherein the head positions at least four transducers simultaneously.

3. A positioner as described in claim 2 wherein the head is moved through the interior of the conduit by attachment to a pipe or stiff rod.

4. A positioner as described in claim 2 wherein the head is pulled through the conduit by a flexible cable means.

5. A positioner as described in claim 1 wherein the shoe itself is made of an abrasion-resistant material.

6. A shoe as described in claim 1 wherein the shoe is made of stainless steel.

* * * * *